United States Patent [19]
Tikkanen et al.

[11] Patent Number: 5,919,640
[45] Date of Patent: *Jul. 6, 1999

[54] STREPTOCOCCUS SUIS ADHESIN PROTEIN AND METHOD FOR PRODUCING IT

[76] Inventors: Kaarina Tikkanen, Maaherrankatu 35 as 9 FIN-70100, Kuopio; Jukka Finne, Katajanokanranta 3 A 5 FIN-00160, Helsinki, both of Finland

[ * ] Notice: This patent is subject to a terminal disclaimer.

[21] Appl. No.: 08/889,013

[22] Filed: Jul. 7, 1997

Related U.S. Application Data

[63] Continuation-in-part of application No. 08/500,895, filed as application No. PCT/FI94/00039, Jan. 28, 1994, Pat. No. 5,716,792.

[30] Foreign Application Priority Data

Jan. 29, 1993 [FI] Finland .................................... 930413

[51] Int. Cl.⁶ .................................................. G01N 33/569
[52] U.S. Cl. .......................... 435/7.34; 424/234.1; 435/6; 536/23.1; 536/24.32
[58] Field of Search .............................. 435/6; 536/23.1, 536/24.32; 424/234.1

[56] References Cited

U.S. PATENT DOCUMENTS

| | | | |
|---|---|---|---|
| 5,059,419 | 10/1991 | Ruehling | 424/165.1 |
| 5,202,113 | 4/1993 | London . | |
| 5,612,042 | 3/1997 | Jacobs | 424/237.1 |

OTHER PUBLICATIONS

Boehncke et al J. of Immunology, vol. 150, 331–341 No. 2 Jan. 1993 The Importance of Dominant Negative Effects of Amino Acid Side Chain Substitution in Peptide–MHC Molecule Interactions and T Cell Recognition.

Medline Express (R) 1996 Appel et al Mol–Divers Oct.; 1996 2(1–2): 29–34 AN 9o7381298 Extensive Mapping studies for seven antigen–antibody interactions have been etc.

Tikkanen et al Infection and Immunity, Sept. 1996, pp. 3659–3665 "The Galactosyl–(α1–4)–Galactose–Binding Adhesin of Streptococcus suis: Occurence in strains of Different Hemagglutination etc".

Tikkanen et al The Journal of Biological Chemistry vol. 270, No. 48, Issue of Dec.1, pp. 28874–28878 1995 "Purification of Galactosyl–α1–4–galactose–binding Adhesin from the Gram–positive Meningitis etc".

Haataja et al The Journal of Biological Chemistry vol. 269, No. 44 Issue of Nov. 4 pp. 27466–27472 1994 "Oligosaccharide–Receptor Interaction of the Galα1–4Ga1 Binding Adhesin of Streptococcus suit".

Dialog Information Services, file 155, Medling, Dialog accession No. 08306030, Medline accession No. 93016030, Liukkonen J. Et al: "Identification of N–acetylneuraminyl alpha 2–3 et al"Oct. 15,1992.

Hemagglutination Activities of Group B,C,D, and G Streptococci: Demonstration of Novel Sugar–Specific et al: Kural et al, pp. 384–389 Infection and Immunity, Feb. 1989, American Society for Microbiology.

"Identification of N–Acetylneuraminyl a2–3 Poly–N–Acetyllactosamine Glycans as the Receptors et al" Liukkonen et al, The Journal of Biological Chemistry, vol. 267, No. 29, Oct. 15, 1992 pp. 21105–21111.

Kural et al, Infect & Immunity, Feb. '89, pp. 384–389.

Elliott, S.P. et al, J. Exp. Med., vol. 145, 1977, pp. 490–499.

Haataja, S et al, J. Biolog. Chem., vol. 268(6), Feb. 25, 1993, pp. 4311–4317.

Mäyrä–Mäkinen, A et al, J of App. Bacteriol., 1983, vol. 55, pp.241–245.

Primary Examiner—James C. Housel
Assistant Examiner—Ginny Allen Portner
Attorney, Agent, or Firm—Nixon & Vanderhye

[57] ABSTRACT

*Streptococcus suis* is a pathogen causing serious disease in pigs. It may also be infectious to man. The *Streptococcus suis* adhesin protein is useful in diagnosis and therapy of said bacteria. Also fragmets of the unique N-terminal part of said protein are immunogenic and can be used in diagnosis an as vaccines. The invention therefore relates to said *S. suis* adhesin protein fragments, antibodies thereto and nucleotide sequences coding for said fragments. The invention further relates to immunoassay and PCR methods for diagnosing *S. suis*.

5 Claims, 1 Drawing Sheet

Figure 1

5´ GAT TCT AAG GCT GTT TTG AAT CAA GCG GTG GCC GAT TTA
TCA GTA GCC CAT TCA ATC CTC CAT CAA GTT CAC TGG TAT
ATG CGT GGT CGT GGC TTT ATG ATT TGG CAT CCA AAG ATG
GAT GAA TAT ATG GAA GAA ATT GAT GGT TAT TTG GAT GAG
ATG AGT GAG CGT TTA ATC ACC TTA GGT GGG GCA CCA TTT
TCT ACC CTT AAA GAG TTT AGT GAA AAT AGT CAG CTC AAG
GAA GTT CTT GGT GAT TAC AAT GTA ACG ATT GAA GAG CAA
TTG GCG CGT GTG GTA GAG GTG TTC CGC TAT CTG GCT GCT
CTT 3´

Figure 2

```
        Asp Ser Lys Ala Val Leu Asn Gln Ala Val Ala Asp Leu Ser Val Ala
                    20                  25                  30

His Ser Ile Leu His Gln Val His Trp Tyr Met Arg Gly Arg Gly Phe
                    35                  40                  45

Met Ile Trp His Pro Lys Met Asp Glu Tyr Met Glu Ile Asp Gly
                    50                  55                  60

Tyr Leu Asp Glu Met Ser Glu Arg Leu Ile Thr Leu Gly Gly Ala Pro
        65                  70                  75                  80

Phe Ser Thr Leu Lys Glu Phe Ser Glu Asn Ser Gln Leu Lys Glu Val
                        85                  90                  95

Leu Gly Asp Tyr Asn Val Thr Ile Glu Glu Gln Leu Ala Arg Val Val
                        100                 105                 110

Glu Val Phe Arg Tyr Leu Ala Ala Leu
                        115             120
```

STREPTOCOCCUS SUIS ADHESIN PROTEIN AND METHOD FOR PRODUCING IT

This application is a continuation-in-part of application Ser. No. 08/500,895, filed Aug. 29, 1995 now U.S. Pat. No. 5,716,792, which is a national stage application of PCT application No. PCT/FI94/00039 filed Jan. 28, 1994, claiming priority of Finnish Application No. 930413 which was filed on Jan. 29, 1993.

BACKGROUND

1. Field of the Invention

The invention relates to a *Streptococcus suis* adhesin protein, biologically or immunologically active derivatives and fragments thereof, a method for producing the adhesin protein, and an antibody raised against the adhesin protein, or the derivative or fragment thereof. The invention also relates to the use of pigeon ovomucoid or a synthetic derivative in the identification of the adhesin protein. The adhesin protein according to the invention, the derivatives and fragments thereof and their antibodies can be used both diagnostically, therapeutically, and prophylactically.

*S. suis* bacteria (the Lancefield group D) are known to cause meningitis, pneumonia, arthritis and sepsis in pigs. *S. suis* type 1 causes mainly septicemia and meningitis in newborn pigs, while type 2 causes meningitis in pigs about 3 to 10 weeks in age, and may also be infectious to humans. There are at least 29 capsular types identified, many of which cause disease in pigs. Concentration of pig breeding and increasing animal densities facilitate the spreading of infections, and infectious diseases caused by *S. suis* become more common. For this reason, the development of a diagnostic technique and a vaccine is of vital importance in the identification and prevention of meningitis and other serious infections. Selective preventive measures directed to pig breeders may also be possible.

2. Prior art

The first event in the establishment of an infectious disease is the adhesion of bacteria to the surface of host cells (Beachey, E. H. (1981) *J. Infect. Dis.* 143, 325–345). The adhesion of bacteria is often mediated by an adhesin protein which occurs on the bacterial surface and adheres specifically to cell surface receptor structures. As a consequence, adhesin is well-suited for the development of a vaccine as the antibodies are directed specifically against a factor necessary for the bacterium; in addition, the specificity allows detrimental side effects to be avoided.

A wide variety of adhesins are known, but in many cases their exact structure and mechanism still remain unknown. They are proteins that recognize the receptors of the host cell specifically, the receptors being usually carbohydrate structures. Various bacterial adhesins and carbohydrate structures recognized by them are described e.g. in Sharon, N., (1987) *FEBS Letters,* 217, 145–157.

*E. coli* and many other gram negative bacteria adhere to specific molecules on the surface of the host cell by lectin-like bacterial adhesins. Usual adhesin receptors include the sugar components of glycolipids and glycoproteins. Adhesins are often attached to hair-like structures called fimbriae (pili) on the surface of the bacterial cell. There are many different types of fimbriae; they vary with respect to both structure and sugar specificity.

As there are often bacterial receptor structures on erythrocytes, bacteria adhere to these structures and agglutinate erythrocytes in vitro. Bacterial cultures may express three or four hemagglutinins (adhesins), each having a different binding specificity. Accordingly, the bacterium is capable of adhering to various cell types.

In enterobacteria studies, adhesion reactions are divided into two main classes: mannose sensitive (MS) reactions in which the hemagglutination reaction is inhibited by α-mannosides, and mannose resistant (MR) reactions in which the hemagglutination cannot be inhibited by α-mannosides. *E. coli* type 1 fimbriae (MS structure) consists almost solely of identical 17 kDa subunits. Several MR adhesins recognize an α-Gal(1-4)-β-Gal structure (P-specific adhesin) or an α-NeuNAc-(2-3)-β-Gal structure (S-specific adhesin). In general, purified fimbriae consist of subunits having a molecular weight varying between 15 and 22 kDa.

Adhesin protein is usually a distinct protein attached to the tips or sides of the fimbriae; it may also be attached directly to the outer membrane of the bacterium. In certain bacterial strains the surface of the bacterial cell contains adhesin protein even in the absence of fimbriae. In such cases, adhesins may form an adhesin capsule around the bacterium. The size of the non-fimbrial adhesins of *E. coli* varies between 13 and 28 kDa (Jann, K. and Hoschutzky, H. (1990), *Current Topics in Microbiology and Immunology* 151, 55–70).

It is known that streptococci bind to various soluble proteins and glycoproteins, whereas their oligosaccharide specificity is mostly unknown. Their specific binding to epithelial cells is also nearly unknown. Certain *Streptococcus sanguis* strains recognize galactose and sialic acid containing structures (Murray, P. A., Levine, M. J., Tabak, L. A., and Reddy, M. S. (1982) *Biochem. Biophys. Res. Commun.* 106, 390–396). The binding of *Streptococcus pneumoniae* to epithelial cells is inhibited by GlcNAcβ1-3Gal (Andersson, B., Porras, O., Hanson, L. A., Lagergard, T., and Svanborg-Eden, C. (1986) *J. Infect. Dis.* 153, 232–237), and this bacterium has been reported to bind to GalNAcβ1-4Gal-containing glycolipids in the lung (Krivan, H. C., Roberts, D. D. and Ginsburg, V. (1988) *Proc. Natl. Acad. Sci., USA,* 85, 6157–6161).

*S. mitis* adheres to the surface of a tooth and contributes to the formation of dental plaque. A sialic-acid-binding adhesin has been successfully isolated from this bacterial strain. The sialic-acid-binding protein had at least two disulphide-bound subunits of 96 kDa and 70 kDa. Both subunits bound N-acetylneuraminic acid-α2-3-galactose-β1-3-N-acetylgalactosamine (Murray, P. A., Levine, M. J., Reddy, M. S., Tabak, L. A., Bergey, E. J. (1986) *Infect. Immun.* 53, 359–365). The galactose-binding adhesin of *S. sanguis* was determined to have a molecular weight of about 20 kDa, and its isoelectric point was in the range 8.5–9 (Nagata, K., Nakao, M., Shibata S., Shizu-kuishi, S., Nakamura R. and Tsunemitsu, A. (1983) *J. Periodontol.* 54, 163–172). In addition to this, a 36-kDa adhesin protein has been cloned from *S. sanguis* bacteria. The carbohydratic specificity of the cloned adhesin remains unknown, whereas it is known that adhesin adheres to saliva-coated hydroxyapatite through the mediation of a pH sensitive receptor (Ganeskumar, N., Song, M. and McBride, B. C. (1988) *Infect. Immun.* 56, 1150–1157).

*S. suis* is an important pathogen in pigs. It colonizes the tonsils or nostrils of piglets and causes serious infections. There are several capsular serotypes, for which reason no vaccine effective against all *S. suis* types is available. The capsular polysaccharides and surface proteins of *S. suis* have been reported to play a role in the pathogenesis, but the molecular mechanism of the infection has remained unknown. Two strains of *S. suis* bacteria have been shown to bind to sialylated poly-N-acetyllactosamine glycans (Liukkonen J., Haataja, S., Tikkanen, K., Kelm, S., and Finne, J. (1992) *J. Biol. Chem.* 267, 21105–21111). However, the hemagglutination caused by most *S. suis* bacteria is inhibited by galactose, so that the galactose-recognizing adhesin is probably more common in *S. suis* bacteria than that mentioned above (Kurl, D., Haataja, S. and Finne, J. (1989) *Infect. Immun.* 57, 384–389).

Several attempts have been made to detach and isolate adhesins by heat treatment and/or extraction. The adhesin of *Proteus mirabilis* was isolated by heat treatment (65° C., 20 min, 50 mM sodium phosphate (pH 7.2) with 2 M urea), and purified by gel filtration (Sepharose CL-4B) (Wray, S. K., Hull, S. I., Cook, R. G., Barrish, J. and Hull, R. A. (1986) *Infect Immun.* 54, 43–49). The lectin of *S. mitis* was separated by extracting the bacteria with lithium-3,5-diiodosalicylate, and a sialic-acid-binding protein was purified from the extract by gel filtration and affinity chromatography (Murray, P. A., Levine, M. J., Reddy, M. S., Tabak, L. A. and Bergey, E. J. (1986) *Infect. Immun.* 53, 359–365). A protein of *Streptococcus pyogenes* (the Lancefield group A) capable of adhering to the cardiac tissue and the basement membrane of kidney cells was successfully separated by treating the bacteria with alkali for 18 h (Stinson, M. W. and Bergey E. J. (1982) *Infect. Immun.* 35, 335–342). A non-fimbrial adhesin of *E. coli* was extracted by heating the bacterial suspension at 65° C. for 30 min (Goldhar, J., Perry, R., Golecki, J. R., Hoschutzky, H., Jann B., and Jann K. (1987) *Infect. Immun.*, 55, 1837–1842). Fimbriae were separated from the fimbrial *E. coli* by mechanical homogenization, and the adhesin protein was separated from the fimbrial homogenate by heat treatment (70° C., 1 h, PBS/5 mM EDTA) (Moch, T., Hoschutzky, H., Hacker, J., Kroncke, K.-D. and Jann, K. (1987) *Proc. Natl. Acad. Sci.* USA 84, 3462–3466) After detachment the adhesin protein has often been precipitated by ammonium sulphate precipitation, whereafter the adhesins have been purified further by various methods. Conventional methods used for the separation of adhesins, however, have not been suitable for the isolation of *S. suis* adhesins.

SUMMARY OF THE INVENTION

The isolation and characterization of the adhesin protein of *Streptococcus suis* have now been performed successfully. The invention thus relates to the adhesin protein or a biologically or immunologically active derivative or fragment thereof, which is characterized in that the adhesin protein binds to the Galα1-4Gal disaccharide structure and comprises the amino acid sequence Ala-Ser-Pro-Ala-Glu-Ile-Ala-Ser-Phe-Ser-Pro-Ala-Pro-Leu-Ala (SEQ ID NO: 1). The adhesin protein according to the invention can be produced by a method wherein the *S. suis* strain is sonicated and the detached adhesin protein is pre-purified by a conventional protein purification technique, and then purified electrophoretically or chromatographically. Pigeon ovomucoid is preferably used in monitoring the purification of the adhesin protein. The invention also relates to antibodies raised against the adhesin protein, or a derivative or fragment thereof, and to a diagnostic method where the antibodies or adhesin protein, or a derivative or fragment thereof are used in an immunoassay method for detecting *S. suis* bacteria or for detecting antibodies directed to *S. suis* bacteria. The invention further relates to the use of the adhesin protein according to the invention or a derivative or fragment thereof as a vaccine, and to the use of the antibodies for passive immunization. In addition, the invention provides nucleotide sequences coding for the adhesin protein fragments of the invention, as well as PCR methods for diagnosis of *S. suis* utilizing said nucleotide sequences as primers.

BRIEF DESCRIPTION OF THE DRAWINGS

FIG. 1 shows a partial DNA sequence of the *S. suis* adhesin protein.

FIG. 2 shows the corresponding partial amino acid sequence of the *S. suis* adhesin protein (amino acid residues 17 to 121).

DETAILED DESCRIPTION OF THE INVENTION

The adhesin protein according to the invention can be detached from the surface of *S. suis* bacteria by sonication. After sonication it is advisable to add a protease-inhibitor to prevent proteolysis. The sonicate is then centrifuged, and the supernatant is recovered. The supernatant containing adhesin protein is preferably pre-purified by a conventional protein purification technique, such as ultrafiltration, dialysis, gel filtration, or precipitation by salt. It is preferable to use ammonium sulphate precipitation, and other proteins can be removed most preferably by an ammonium sulphate solution having a saturation degree of about 60%, whereafter the adhesin protein can be precipitated by an ammonium sulphate solution having a saturation degree of about 70%.

The actual purification may be carried out electrophoretically, e.g. by gel electrophoresis, or chromatographically, e.g. by affinity chromatography or immunoaffinity chromatography. Preferably a preparative native gel electrophoresis is applied. The native electrophoresis means an electrophoresis without sodium dodecyl-sulphate (SDS). It is particularly advantageous to use a continuous elution electrophoresis apparatus preferably cylindrical in shape. Fractions are collected from the apparatus and protein fractions having adhesin activity are recovered.

The biological activity of the adhesin protein of *S. suis* can be utilized in monitoring the purification of the adhesin protein. The adhesin protein is associated with the hemagglutination ability of *S. suis* bacteria, which can be inhibited by certain sugar compounds, such as by galactose and N-acetylgalactosamine or by galactose only, at millimolar concentrations. In the study of galactose-specific adhesin proteins, it is preferable to use sialidase-treated human erythrocytes. Hemagglutination tests and hemagglutination inhibition tests are described in Kurl, D. N., Haataja, S. and Finne J. (1989) *Infect. Immun.* 57, 384–389; and Haataja, S., Tikkanen, K., Liukkonen, J., Francois-Gerard, C. and Finne, J., (1993) Characterization of a Novel Bacterial Adhesion Specificity of *Streptococcus suis* Recognizing Blood-Group P Receptor Oligosaccharides, *J. Biol. Chem.* 268, No 6, p. 4311–4317 (1993).

Inhibition studies with mono- and oligosaccharides show that the receptor structure of *S. suis* is Galα1-4Galβ1-4Glc. This forms the oligosaccharide part in the P$^k$ antigen of the blood group P glycolipids. On the other hand, hemagglutination inhibition tests and direct binding of glycoproteins and neoglycoproteins indicate that the P$_1$ antigen structure Galα1-4Galβ1-4GlcNAc is also recognized by the adhesin. Consistent with this, the adhesin binds strongly to the Galα1-4Gal disaccharide structure as compared with the α1-3, α1-6, α-galactose disaccharide derivatives. Inhibition studies with oligosaccharides show that the terminal α-galactose plays an important role in the binding of adhesin.

It has now been found out that pigeon ovomucoid is an extremely effective inhibitor. 0.06 µg/ml of pigeon ovomucoid inhibits the hemagglutination induced by the *S. suis* strain 628 completely. Pigeon ovomucoid is a glycoprotein the terminal sequence of the glycan chains of which is Galα1-4Galβ1-4GlcNAc; it is described in Francois-Gerard, C., Gerday, C. and Beeley, J. G. (1979) *Biochem. J.*, 117, 679–685. This structure causes the *S. suis* adhesin protein to bind strongly to pigeon ovomucoid. Consequently, the pigeon ovomucoid also has the blood-group $P_1$ activity. Synthetic derivatives containing the Galα1-4Gal disaccharide structure can also be used in the identification of *S. suis* adhesin protein. E.g. Galα1-4Galβ1-4Glc-O-CETE-BSA- (O-CETE-BSA is O-2-(2-carbomethoxyethylthio) ethyl bovine serum albumin, manufactured by Arlöv in Sweden) has proved to be an extremely strong inhibitor in the hemagglutination inhibition.

The purification of the adhesin protein can be easily monitored by a simple pigeon ovomucoid binding test. The ovomucoid used in monitoring the purification may be labelled e.g. by a radioactive label. The test may be e.g. a spot test where a sample containing adhesin protein is pipetted onto a nitrocellulose paper, and the paper is then covered with the radioactively labelled pigeon ovomucoid, incubated, and washed. The radioactivity bound to the paper is then determined. The intensity of the binding correlates with the hemagglutination activity of the strain.

Preferably the purification of the adhesin protein is monitored by the Western blot method, where the samples are subjected to a polyacrylamide gel electrophoresis, after which the proteins are transferred by an electric current onto a membrane which is then treated in a similar manner as the paper above. The *S. suis* sonicates from the different strains exhibit a single adhesin protein band moving at the same rate. The intensity of the band correlates with the hemagglutination activity. The band is also distinguishable when the hemagglutination-negative strains are used, though usually more weakly. A reason for this might be the phase variation associated with the adhesin protein, i.e. bacteria may express adhesin at a different level in different conditions. Another possible reason is the inhibitory effect of other surface structures, such as a capsule.

The above-described method allows the production of a *S. suis* adhesin protein which has a molecular weight of about 18,000, an isoelectric point of about 6.4, the N-terminal sequence of which is Ala-Ser-Pro-Ala-Glu-Ile-Ala-Ser-Phe-Ser-Pro-Ala-Pro-Leu-Ala (SEQ ID NO: 1), and the amino acid composition of which is:

| Amino acid | mol amino acid/mol protein |
|---|---|
| Asx = asparagine and/or asparaginic acid | 13 |
| Thr = threonine | 8 |
| Ser = serine | 6 |
| Glx = glutamine (Glu) and/or glutamic acid | 26 |
| Gly = glycine | 22 |
| Ala = alanine | 17 |
| Val = valine | 10 |
| Cys = cysteine | 0 |
| Met = methionine | 4 |
| Ile = isoleucine | 11 |
| Leu = leucine | 12 |
| Tyr = tyrosine | 4 |
| Phe = phenylalanine | 6 |
| Lys = lysine | 16 |
| His = histidine | 7 |

-continued

| Amino acid | mol amino acid/mol protein |
|---|---|
| Arg = arginine | 7 |
| Pro = proline | 12 |

In addition to the biological activity described above, the adhesin protein is immunologically active, i.e., it elicits the formation of antibodies. It is present in *S. suis* strains independently of the capsular serotype.

The invention thus also relates to the derivatives and fragments of the above-described adhesin protein, which have essentially the same biological or immunological activity as the adhesin protein. A derivative signifies a protein in which part of the amino acids have been substituted, deleted or added, but which nevertheless has retained its essential biological or immunological properties. Substituting or added amino acids include both amino acids occurring in proteins and derivatives of such amino acids. The derivatives according to the invention also include possible aggregates. A fragment signifies a portion of the adhesin protein described, which has retained its essential biological or immunological properties. The derivatives and fragments can be prepared in a manner conventional in protein chemistry. Fragments are preferably prepared by a peptide synthesis e.g. by the solid-phase method. The adhesin and its derivatives or fragments can also be produced by the methods of gene technology.

The invention thus provides a fragment of the *Streptococcus suis* adhesin protein, which fragment comprises a sequence of at least four or preferably at least five amino acids from the amino acid sequence Ala-Ser-Pro-Ala-Glu-Ile-Ala-Ser-Phe-Ser-Pro-Xaa-Pro (SEQ ID NO: 2), wherein Xaa is alanine or arginine, and which fragment elicits antibodies specifically binding to a *Streptococcus suis* adhesin protein having a molecular weight of about 18,000 and binding to the Galα1-4Gal disaccharide structure. Preferably said fragment comprises a sequence of at least four amino acids from amino acid residues 1 to 11 of SEQ ID NO 2. Usually the fragment is not longer than about twenty and preferably not more the sixteen amino acids.

More specifically, the invention provides an immunologically active fragment of *Streptococcus suis* adhesin protein, said adhesin protein having a molecular weight of about 18,000 and binding to the Galα1-4Gal disaccharide structure, and said fragment comprising an amino acid sequence which essentially is Ala-Ser-Pro-Ala-Glu-Ile-Ala-Ser-Phe-Ser-Pro-Xaa-Pro (SEQ ID NO: 2), wherein Xaa is alanine or arginine. "Essentially" in this connection means that one or a few amino acids may be deleted, substituted or added provided that the fragment still elicits antibodies specifically reactive with the *S. suis* adhesin protein disclosed. Especially conservative substitutions are possible. In one embodiment of the invention said immunologically active fragment of the adhesin protein comprises at least SEQ ID NO: 2, and in another embodiment of the invention it is SEQ ID NO: 2.

The invention further relates to antibodies raised against the adhesin protein or to fragments or derivatives thereof. In this connection, such antibodies also include antibody fragments, such as Fab fragments, or antibody portions expressed in phages which bind to the adhesin protein according to the invention, its derivative or fragment. Antibodies include both polyclonal and monoclonal antibodies.

Due to its immunological properties the adhesin protein according to the invention, and the derivatives and fragments thereof are also usable as immunogenic compositions e.g. as a vaccine against diseases caused by S. suis bacteria, such as septicemia and meningitis in pigs. The vaccine may also contain a polynucleotide coding for the corresponding sequences, optionally in the form of a recombinant organism. The use as a vaccine for humans may also be possible e.g. in the case of groups at risk, such as pig breeders or slaughter workers. Still another possible use of the antibodies would be in passive immunization.

The invention also relates to diagnostic methods for detecting S. suis bacteria or for detecting antibodies directed to S. suis bacteria by utilizing immunoassay methods known per se, such as immunofluorescence, ELISA and RIA techniques. To detect the presence of S. suis bacteria in a sample, the sample is contacted with the antibody according to the invention, and the obtained antigen-antibody complexes are then analyzed. Correspondingly, it is possible to detect antibodies directed to S. suis bacteria by reacting the suspected sample with the adhesin protein according to the invention, or a derivative or fragment thereof and analyzing the obtained antigen-antibody complexes. The antigen-antibody complexes may be analyzed either directly or indirectly in a wide variety of ways well-known to one skilled in the art. It is a common practice to immobilize either the antigen or the antibody.

Homology studies have proved that the twenty N-terminal amino acids of the S. suis adhesin protein are unique for S. suis and therefore adhesin protein fragments from this N-terminal part of the protein provide an excellent means for specific diagnosis of and immunization with S. suis. Accordingly the invention provides an immunoassay method of detecting S. suis bacteria, comprising the steps of a) contacting a sample with said antibodies, and b) analyzing the antigen-antibody complexes obtained, the formation of the antigen-antibody complexes indicating the presence or amount of S. suis in the sample. Further, the invention provides an immunoassay method of detecting antibodies to S. suis bacteria, comprising the steps of a) contacting a sample with the adhesin protein fragment described, and b) analyzing the antigen-antibody complexes obtained, the formation of the antigen-antibody complexes indicating the presence or amount of antibodies to S. suis in the sample.

The isolation and purification of the S. suis adhesin protein also made it possible to detect S. suis using the polymerase chain reaction (PCR), which is described e.g. in Erlich H. A. (ed.) (1989) PCR Technology: Principles and Applications for DNA Amplification, Stockton Press; and Innis M. A., Gelfand D. H., Sninsky J. J. & White T. J. (eds) (1990) PCR Protocols: A Guide to Methods and Applications. Academic Press, New York. Appropriate primer pairs were constructed based on known amino acid sequences of the protein. After amplification the nucleotide sequence of the amplified fragment of the adhesin protein could be determined and used for constructing further primers. By using an oligonucleotide derived from at least part of the specific N-terminal sequence as one primer, PCR provides an excellent tool for diagnosing S. suis. The other primer is chosen from the complementary strand towards the C-terminal end of the protein. Thus the invention provides a PCR method for detecting S. suis bacteria, comprising the steps of a) contacting a sample with a primer pair comprising an oligonucleotide which codes for at least part of the adhesin protein fragment of the invention or which is complementary thereto, and b) amplifying the region between the primers, and c) detecting the amplification product, thereby indicating the presence or amount of S. suis in the sample. The invention further includes the nucleotide sequences useful in the method.

The following non-restrictive examples illustrate the invention.

EXAMPLE 1

Growing *Streptococcus suis* bacteria

The following S. suis strains were used in the studies:
Hemagglutinating: 628, TEW/2, R75/L1, 825 and 752
Non-hemagglutinating: 3027, 1045 and 598/T5

The strains 628, TEW/2, R75/L1 and 825 are described in Kurl, D. N., Haataja, S. and Finne, J., (1989) *Infect. Immun.* 57, 384–389. The other strains were obtained from Dr. J. Hommez, Regional Veterinary Investigation Laboratory, Torhout, Belgium.

The strains were stored frozen in Todd-Hewitt medium at −20° C. The bacteria were grown anaerobically (Gas Pak system) on fresh sheep blood agar plates at 37° C. overnight. The bacteria were harvested from the plates and suspended in phosphate buffer A (10 mM sodium phosphate buffer, 0.15 M NaCl, pH 7.4) adjusted to a concentration that gave an $A_{600nm}$ 0.5 at 1:100 dilution.

EXAMPLE 2

Purification of adhesin protein

Adhesin protein was detached from the bacterial surface by sonicating 5×15 sec. (chilling on ice for 1–2 min) in 2.5 ml batches into phosphate buffer A. After sonication, protease inhibitor PMSF (phenylmethylsulphonyl fluoride) was added to a 2 mM concentration. The sonicates were centrifuged at 15,800×g, +8° C., and the supernatants were recovered. The adhesin protein was pre-purified from the mixture by a fractionating ammonium sulphate precipitation. 16 ml of the supernatant was used in the ammonium sulphate precipitation. Other proteins were removed from the mixture by ammonium sulphate having a saturation degree of 60%, and adhesin was precipitated by ammonium sulphate having a saturation degree of 70%. No significant amounts of adhesin protein remained in the 70% supernatant. Cold saturated ammonium sulphate was pipetted into the solution (0° C.), the solution was allowed to stand for 1 h in ice bath, and then centrifuged at 15,800×g, 20 min. Deposits from the 70% precipitation were recovered and dissolved in 16 ml of phosphate buffer B (3.3 mM sodium phosphate buffer, 0.05 M NaCl, pH 7.4). The deposits were dialysed overnight at +8° C. against $H_2O$, lyophilized, and dissolved in 4 ml of phosphate buffer A. The purification was monitored in a 6% native polyacrylamide gel electrophoresis by pigeon ovomucoid labelled with radioactive iodine in a Bio Rad minigel device (see Example 3).

The actual purification was performed in a Bio Rad 491 Prep Cell preparative electrophoresis device. 6% native polyacrylamide gel was poured into the cylindrical gel device (the height of the separating gel was 6 cm and that of the stacking gel 2 cm). The total volume of the sample was 4 ml, containing 3,000 μl of the protein solution prepared above, 920 μl of sample buffer (no SDS solution), and 80 μl of staining dye BPB (bromophenol blue). The running solution was 25 mM Tris-192 mM glycine, pH 8.3, and the elution buffer was Tris-HCl, pH 8.3. 4 ml fractions were extracted from the samples, and the fractions were analyzed by measuring their absorbancy at two different wave lengths (214 nm and 280 nm), whereafter the samples were subjected to polyacrylamide gel electrophoresis in the Bio Rad minigel device, as described in Example 3. Fractions 79–83 contained adhesin protein. Fractions 79–81 were combined, dialyzed overnight at +8° C. against phosphate buffer B, and freeze-dried. The dried precipitate was kept at −20° C. for subsequent analyzing.

EXAMPLE 3

Monitoring the purification

The monitoring of the purification process was based on the observation that *S. suis* bacteria bind intensively pigeon ovomucoid, which contains the galactocyl-α1-4-galactoside of the disaccharide structure. For this reason, an adhesin protein identification method was developed by labelling pigeon ovomucoid radioactively with $^{125}I$ label. In the binding test of the radioactively labelled ovomucoid, the negative, i.e. non-hemagglutinating *S. suis* strain 598/T5 and the weakly hemagglutinating *S. suis* strain 825 were used as control strains in addition to the hemagglutinating *S. suis* strain 628 (the hemagglutination titer of the *S. suis* strain 628 was 64, the titer of the strain 825 was 4, and the titer of the strain 598/T5 was 0). The ovomucoid was labelled radioactively with the $^{125}I$ isotope by the Iodo-Bead method (Pierce Chemical Co, Rockford Ill.) in accordance with the instructions of the manufacturer.

At the first stage, a spot test was developed. In this binding test each bacterial suspension prepared as described in Example 1 was diluted (1:1; 1:10; 1:50) in phosphate buffer A. 1 μl of the suspensions was pipetted onto a gridded nitrocellulose paper, whereafter all extra binding sites were covered by incubation for 1.5 h in phosphate buffer C (0.1 M sodium phosphate buffer, 0.5% Tween 20, 150 mM NaCl, pH 5.3). The nitrocellulose was then covered with the $^{125}I$ ovomucoid (about 6×10$^5$ cpm, specific activity about 2.5× 10$^5$ cpm/μg ovomucoid), and incubated for 1 h at +8° C. The membrane was washed 3×10 min in phosphate buffer C, dried between filter papers and exposed to an X-ray film at −80° C. for 24 h. Binding could be detected only in the hemagglutinating strains even at low bacterial concentrations, in addition to which the binding intensity correlated with the hemagglutinating activity.

At the second stage, by applying the above-described method, a Western blot identification method was developed for the adhesin protein in a polyacrylamide gel electrophoresis (Laemmli, U. K. (1970) Nature (London) 227, 680–685). A native gel electrophoresis was used without SDS addition so that the proteins retained their native form. Bacterial sonicates prepared as described in Example 2 were separated in a number of polyacrylamide gel electrophoresis systems containing different concentrations of polyacrylamide (5–9%). Finally the concentration of 6% was used. After the separation the sonicates were transferred by an electric current (60 mA, 30 min) to a PVDFp (Millipore) membrane (Burnette, W. N. (1981) *Anal. Biochem.* 112, 195–203), and the membrane was labelled with the $^{125}I$ ovomucoid as described above. The hemagglutinating *S. suis* strains used in the tests were: 628, TEW/2, R75/L1, 825, 752. The non-hemagglutinating strains were: 3027 and 1045. The sonicates of the hemagglutinating bacterial strains visualized one strong protein band which moved in the electrophoresis at the same rate. The intensity of the band correlated with the hemagglutination activity. However, the negative strains also visualized a band moving at the same rate in the native gel electrophoresis, usually more weakly. The band was thus present in all *S. suis* strains and was not related to the capsular serotypes.

EXAMPLE 4

The molecular weight of the adhesin protein and the checking of purity

The purity of adhesin was checked, and the molecular weight was determined on the basis of the electrophoretic mobility in a 15% SDS polyacrylamide gel electrophoresis (Laemmli, U. K. (1970) *Nature* (London) 227, 680–685). The adhesin protein of the strain 628 (4 μg) was boiled for 5 min in a 2% SDS solution containing either 5% mercaptoethanol or 2.5 mM dithiotreitol. A single band was distinguishable in the purified adhesin protein. Standard proteins Low Molecular Weight Standards manufactured by Pharmacia were used as molecular weight standards. The molecular weight of adhesin was determined to be 18,000.

EXAMPLE 5

Isoelectric point

Isoelectric focusing was performed in a Phast gel electrophoresis device with the Phast isoelectric system (Pharmacia). The gel was Phast Gel 15531 3-9, and the standards were IEF standard 3-10 (Pharmacia). 0.2 μg of purified adhesin of the strain 628 were used in the determination. The isoelectric focusing gel was stained by using Silver IEF-Method 6 of the Phast system. The isoelectric point of adhesin was determined to be 6.4.

EXAMPLE 6

Amino acid analysis

For the amino acid analysis, 7 nmol of purified adhesin of the strain 628 was dissolved in 100 μl of 6 M HCl solution. 60 nmol norleucine was added as an internal standard. The solution was hydrolyzed at 110° C. for 24 h, freeze-dried, and analyzed with the LKB 4151 Alpha Plus Aminoacid Analyzer according to the instructions of the manufacturer.

The amino acid composition was as follows:

| | Amino acid | mol amino acid/mol protein |
|---|---|---|
| 1 | Asx | 13.2 |
| 2 | Thr | 8.1 |
| 3 | Ser | 5.8 |
| 4 | Glx | 26.4 |
| 5 | Gly | 22.3 |
| 6 | Ala | 16.9 |
| 7 | Val | 10.3 |
| 8 | Cys | 0.0 |
| 9 | Met | 3.9 |
| 10 | Ile | 11.4 |
| 11 | Leu | 12.3 |
| 12 | Tyr | 3.9 |
| 13 | Phe | 6.0 |
| 14 | Lys | 15.9 |
| 15 | His | 6.6 |
| 16 | Arg | 6.8 |
| 17 | Pro | 12.4 |

EXAMPLE 7

The N-terminal amino acid sequence of the adhesin protein

The N-terminal amino acid sequence of the adhesin protein was determined in the Applied Biosystems 477A Pulsed Liquid Protein/Peptide Sequencer with 120A Amino Acid Analyzer in accordance with the manufacturer's instructions. Purified adhesin was run into a 6% native polyacrylamide gel, from which the adhesin was transferred by an electric current into a PVDFp membrane as described in Example 3. The membrane was stained by the protein dye Coomassie Brilliant Blue (10 min), excessive dye was removed and the protein band was cut off for peptide sequencing.

The N-terminal sequence of the adhesin protein was also determined successfully from the supernatants of the sonicated bacteria: The mobility of the adhesin protein in the native gel electrophoresis is known as the adhesin protein band can be identified on the PVDFp membrane by utilizing the $^{125}$I pigeon ovomucoid. The mobility of the adhesin protein was identified from the five different hemagglutinating S. suis strains (628, TEW/2, R75/L1, 825, 752) in a 6% native polyacrylamide gel electrophoresis; the sonicates of these bacterial strains were subjected to electrophoresis, and the bands were transferred onto a PVDFp membrane. The adhesin bands were cut off from the membrane for amino acid sequencing as described above. The obtained N-terminal sequence was identical for all strains, that is: Ala-Ser-Pro-Ala-Glu-Ile-Ala-Ser-Phe-Ser-Pro-Ala-Pro-Leu-Ala (SEQ ID NO: 1).

EXAMPLE 8

Production of antibodies against the adhesin protein of strain 628

Antibodies against the adhesin protein of the strain 628 were produced in Balb/c mice. The mice were immunized either with pure adhesin (10 μg/mouse) or with the sonicate of S. suis (80 μg/mouse). In the former case the adhesin was injected twice in Freund's complete adjuvant (F.C.A.) and once in Freund's incomplete adjuvant (F.I.C.A.). In the latter case the protein mixture was injected into the mice once with F.C.A. and twice mixed with F.I.C.A. The immunization was performed subcutaneously. In both cases, antibodies against the adhesin protein were elicited.

The antibody formation was studied on a PVDFp membrane, onto which the sonicate supernatants of S. suis had been transferred (see Example 2). The band of the adhesin protein was identified (cf. Example 3). (Nonspecific binding of the antibodies was prevented by incubating the membrane for 1.5 h in a 1.5% milk powder-0.5% Tween 20 solution in buffer D (10 mM Tris, 150 mM NaCl, pH 7.8). The membrane was washed trice in buffer D, to which 0.05% Tween 20 had been added. The antibody dilutions were added for one hour, whereafter the membrane was washed five times in buffer D, to which 0.05% Tween 20 had been added. The membrane was incubated with anti-mouse antibody labelled with alkaline phosphatase for one hour (1:1,000 dilution), washed five times in buffer D, and the substrate of alkaline phosphatase was added to effect a colour reaction (bromochloroindolyl phosphate/nitro blue tetrazolium). The formation of antibodies against the S. suis strain 628 was strong. The antibodies were still able to specifically recognize the adhesin protein even at a dilution of 1:5×10$^5$.

EXAMPLE 9

Polyclonal and monoclonal antibodies to the adhesin and to a fragment thereof

Polyclonal and monoclonal antibodies. The adhesin was purified as described before. BALB/c mice were immunized subcutaneously with pure adhesin (6 to 10 μg) twice with complete and once with incomplete Freund's adjuvant (FICA) at 3-week intervals and then given booster injections monthly. Peripheral blood samples were collected for polyclonal antisera. Monoclonal antibody was produced as described by Köhler, G., and C. Milstein. 1975, Nature (London) 256:495–497 and Gefter, M. L., D. H. Margulies, and M. D. Scharff. 1977. Somatic Cell. Genet. 3:231–236. Three days after the first booster injection, spleen cells were removed and fused with myeloma line Sp2/0 in polyethylene glycol 1500. The resulting hybridomas were screened by Western blot (immunoblot) analysis against a sonication extract of S. suis 628. The cells were cloned by limiting dilution, grown by hybridoma growth factor supplement, and retested for antibody activity. Culture supernatants from the clones which continued to show a positive reaction were tested in Western blot and hemagglutination inhibition assays.

Antibodies to synthetic peptide. A peptide Ala-Ser-Pro-Ala-Glu-Ile-Ala-Ser-Phe-Ser-Pro-Ala-Pro-Cys (SEQ ID NO: 2+ Cys) was contructed according to the N-terminal amino acid sequence of the adhesin with an additional cysteine residue for coupling. The synthesis was carried out by the solid phase method using Applied Biosystems 431A Automated Peptide Synthetizer and Fmoc Strategy. The peptide was coupled to keyhole limpet hemocyanin by the maleimidobenzoyl-N-hydroxysuccinimide method, using 150 μg of peptide and 2.8 mg of hemocyanin (Liu, F.-T., M. Zinnecker, T. Hamaoka, and D. H. Katz. 1979. Biochemistry 18:690–697). Polyclonal antibodies against the synthetic peptide antigen were produced by immunizing a New Zealand White rabbit seven times with 625 μg of the conjugate in Freund's incomplete adjuvant at 3- to 6-week intervals.

Western blot analysis. Antibody formation was studied on a PVDF-P membrane, with proteins transferred from gels as described above.

EXAMPLE 10

Characterization and use of the antiboties

Polyclonal adhesin antibodies induced by immunization with the pure adhesin specifically recognized one single band in extracs of S. suis in Western blot analysis. The band had the same mobility as the band which binds radiolabeled pigeon ovomucoid. A monoclonal antibody (E10G3) to the adhesin also recognized a band with the same mobility.

The polyclonal antiserum specifically inhibited the hemagglutination induced by S. suis down to a dilution of 1:3,200. The E10G3 monoclonal hybridoma culture medium exhibited low inhibitory activity with a titer of 1:20.

Probing for the presence of adhesin in S. suis strains by using pigeon ovomucoid and adhesin antibodies. To probe for the presence of the adhesin in different S. suis strains, both pigeon ovomucoid and polyclonal adhesin antibodies were used. Western blot analysis with the adhesin antibodies of the extracts of all S. suis strains investigated revealed a single band with the mobility of the adhesin. Probing of the membranes with radiolabeled pigeon ovomucoid indicated that the same band also exhibited Galα1-4Gal-binding activity and thus confirmed its identity as the adhesin. Slight differences in the mobilities of the adhesin band in different strains were observed, which suggests possible differences in the primary structure or posttranslational modification of the adhesin.

Comparison of hemagglutination activity and the amount of adhesin. To evaluate whether the differences in the agglutination activities of diffenrent S. suis strains could be due to differences in the expression of adhesin, the amounts of adhesin detected with polyclonal antibodies in the Western blots were compared with the hemagglutination activities (Table 1).

TABLE 1

Hemagglutination activities and adhesin expression in *S. suis* strains of different serotypes and under different stages of phase variation.

| Strain[a] | Serotype | Hemagglutination[b] | Adhesin[c] |
|---|---|---|---|
| 836 | 1 | 256 | ++++ |
|  |  | 32 | +++ |
| 628 | 2 | 256 | ++++ |
|  |  | 32 | ++ |
| 877 | 2 | 8 | ++++ |
|  |  | 2 | ++ |
| TEW/2 | 2 | 64 | ++++ |
|  |  | 0 | ++++ |
| 652 | 1 | 1 | +++ |
| B565 | 1 | 2 | ++++ |
| 663 | 2 | 2 | ++++ |
| BA 41/8 | 2 | 4 | + |
| R75/L1 | 2 | 1 | +++ |
| 825 | 4 | 1 | + |
| BA 71/4 | 4 | 4 | + |
| 849 | 4 | 2 | + |
| 598 | 5 | 0 | ++ |
| B121 | 7 | 0 | ++++ |
| B463 | 7 | 0 | +++ |
| 752 | 7 | 1 | +++ |
| BA 33/8 | 8 | 0 | + |
| BA 39/3 | 8 | 4 | ++ |
| B154 | NT[d] | 1 | + |
| B295 | NT | 0 | + |
| 851 | NT | 0 | +++ |
| 875 | NT | 0 | + |
| 878 | NT | 8 | + |

[a]The agglutination propertics of the strains are described in Kurl, D. N., S. Haataja, and J. Finne. 1989. Infect. Immun. 57:384–389; The first four strains were analyzed under a high- and a low-hemagglutinating phase.
[b]Reciprocal of the hemagglutination titer.
[c]The amount of adhesin was estimated from duplicate Western blots, using polyclonal adhesin antibodies; synthetic peptide antibodies against the N-terminus of the adhesin gave similar results.
[d]NT, nontypeable.

When polyclonal antibodies to the synthetic N-terminal peptide were used, the amounts correlated with those determined with the polyclonal adhesin antibodies, which suggested that the N termini did not antigenically differ significantly in the different strains. The N-terminal peptide and antibodies raised thereto can therefore be used diagnostically for detecting *S. suis*.

The adhesin was detected by Western blotting in all 23 strains examined, including several nonhemagglutinating strains and strains examined under a weak hemagglutination or a nonhemagglutination phase. The adhesin was also present independent of the serotypes, which included the main pathogenic types.

In spite of the slight mobility differences, immunoblot analysis with the polyclonal antibodies, monoclonal antibody, and antibodies to the synthetic N-terminal peptide, as well as probing with radiolabeled pigeon ovomucoid, all gave comparable estimates on the amount of the adhesin in the different strains, which indicated that the Galα1-4Gal-binding adhesins are closely related in structure and antigenicity. The twenty N-terminal amino acids of the adhesin protein are unique for *S. suis*. Amino acid residue 12 may be arginine.

EXAMPLE 11

Bactericidal tests

Adhesin as antigen. In the tests were used mice (Balb/c) which had been immunized with purified adhesin in Freund's incomplete adjuvant as described in Example 9. The mice produced opsonic antibodies to *S. suis* bacteria. Non-immunized mice not showing opsonic activity to *S. suis* bacteria were used as controls. The bactericidal tests were carried out by modifying a method earlier described for pigs (Agarwal, K., Elliott, S. D. and Lachman, P. J. (1969) "Streptococcal infection in young pigs III. The immunity of adult pigs investigated by the bactericidal test", Journal of Hygiene 67, 491).

Methods. About 1 ml of blood was recovered from both the immunized and non-immunized mice into heparin vials (15 units litium-heparin/0.01 ml phosphate buffer A) by heart puncture. The fresh heparin blood was divided into aliquots of 300 μl and put in sterile vials having a screw cap. Into each vial, 33 μl of fresh culture was inoculated from the logaritmic growth phase of *S. suis* strain 628 (serotype 2). Immediately after the inoculation, a sample of 80 μl was plated from the vials onto sheep blood agar plates for the colony count (2 parallel plates). The vials were incubated at 37° C. in a shaker for 3.5 h and then an 80 μl sample was taken from each vial for plating onto sheep blood agar plates for determining the colony count. The sheep blood agar plates were incubated anaerobically (Gas Pak) at 37° C. for 20 hours, after which the colonies were counted. The results are shown in Table 2.

TABLE 2

The growth of *S. suis* bacteria (colony count) in the blood of the mice, when about 3 000 bacterial cells/333 μl were added.

|  | Colony count/80 μl | |
|---|---|---|
|  | 0 h | 3.5 h |
| Immunized mice No. |  |  |
| 1 | 598 | 84 |
| 2 | 718 | 45 |
| Control mice No. |  |  |
| 3 | 1036 | >2000 |
| 4 | 984 | >2000 |

The results show that the blood of the mice immunized with adhesin is bactericidal to *S. suis* bacteria, which indicates its effect as a vaccine.

A synthetic N-terminal peptide as antigen

Opsonic antibodies raised against a synthetic N-terminal peptide were examined from rabbit and mouse blood. A peptide was constructed and the immunization of the rabbit was carried out as described in Example 9. The mouse was immunized with 150 μg of the antigen mixture eleven times in FICA at three week intervals. The inoculation amounts were 10 000 bacterical cells to 1 ml rabbit blood (1000 cells/100 μl) and 1500 cells to 300 μl mouse blood (500 cells/100 μl).

The bactericidal assay was carried out as described for adhesin above. Also the N-terminal fragment development bactericidal activity indicating its effect as a vaccine. (Table 3)

TABLE 3

Bactericidal activity of mouse and rabbit
blood after immunization with the
synthetic N-terminal peptide antigen

| | | CFU/100 µl | |
|---|---|---|---|
| [a]Animal | Aimed inoculum | At 0 h | At 3.5 h |
| Non-immunized | | | |
| Rabbit | $1.0 \times 10^3$ | 880 | >2000 |
| Mouse | $0.5 \times 10^3$ | 494 | >2000 |
| Immunized | | | |
| Rabbit | $1.0 \times 10^3$ | 674 | 229 |
| Mouse | $0.5 \times 10^3$ | 458 | 187 |

[a]Blood from non-immunized animals or animals immunized with the synthetic peptide antigen constructed according to the N-terminal amino acid sequence of the S. suis adhesin was collected and mixed with living strain 628 bacteria. Samples were taken immediately after inoculation and after incubation at 37° C. for 3.5 h. The values are means from two plates.

EXAMPLE 12

PCR diagnostics

The N-terminal sequence specific for the *S. suis* strains was used to detect *S. suis* bacteria specifically by PCR. Routine DNA manipulations were performed as described by Maniatis et al., 1989, Molecular cloning: a laboratory manual: Cold Spring Harbor Laboratory, Cold Sring Harbor, N.Y.

Two oligonucleotides were constructed one of which is based on the NH$_2$-terminal amino acid sequence and the other obtained more towards the C-terminal end of the adhesin protein after trypsinization of the adhesin and sequencing the tryptic peptides obtained. DNA amplification was carried out using these two primer pairs and chromosomal DNA from *S. suis* strain as a template.

Oligonucleotides (I):

Based on residues 2–7 of the N-terminal amino acid sequence:

5' TCI/AGI-CCI-GCI-GAA/G-ATI-GC 3' (SEQ ID NO: 3)
(Ser-Pro-Ala-Glu-Ile-Ala)

Based on a sequenced peptide from the trypsinization:
5' TC-IGA-NAC-A/GTC-A/GAA-NCC 3' (SEQ ID NO: 4)

I is inosine and N is A,T,G or C. The sequence listing is made up according to the IUPAC-IUB standard (Nucleic Acids Research, 13, 3021–3030 (1985)).

PCR Procedure

Oligonucleotides prepared were diluted in H$_2$O to a concentration of 20 pmol/µl. The bacteria were cultured in Todd-Hewitt broth (Difco) for 18 hours and collected by centrifugation. Bacterial suspensions were prepared as described before. The suspensions were further diluted 1/10 in sterile water and used in PCR as a template source. In PCR amplification DNA polymerase and all the reagents were purchased by Dynazyme, Finnzymes Oy, Finland.

First the following reagents were mixed (I mix): 5 µl of 10× buffer, 4 µl of (both) the oligonucleotides and 13 µl of sterile water. DynaWax was melted in water bath (60° C.). Then the following reagents were mixed (II mix): 1 µl of 1×dNTP (nucleotides), 22 µl of sterile water, 1 µl of DNA polymerase. After this the reaction mixtures were prepared: 25 µl of I mix, 1 µl of bacterial suspension, 2 drops of DynaWax and 23 µl if II mix. The following program was used:

| step 1 | | | 94° C. | 2 | min |
|---|---|---|---|---|---|
| step 2 | | | 94° C. | 40 | s |
| step 3 | | | 42° C. | 30 | s |
| step 4 | | | 72° C. | 1 | min |
| step 5 | GOTO2 | 34 x | | | |
| step 6 | | | 72° C. | 5 | min |
| step 7 | End | | | | |

Agarose gel electrophoresis

PCR products (20 µl) were analysed in agarose gel (0.75–2% agarose in TAE-buffer) (TAE-buffer: 4.8 g Tris and 0.37 g EDTA in 1l of water, pH 8.0 set with glacial acetic acid) electrophoresis and DNA-molecular weight standards (RsaI and HinfI cut pUC 19)were run in parallel. Running buffer: TAE/ethidiumpromide 0.5 µg/ml. Running conditions: 96 V.

Sequencing of the PCR product

The PCR-product was then cloned into a plasmid. The PCR product was purified (Geneclean II, BIO 101, Inc., USA) and cloned into a vector (pCR™II Vector, TA-Cloning Kit, In Vitrogen, The Netherlands) and *E. coli* strain LE 392 was transformed. Positive clones were selected and cultured. DNA was purified (Wizard Minipreps, Promega Corp. USA) and sequenced and analyzed (A.L.F. automated DNA sequenzer, Pharmacia, Sweden). The DNA sequence is shown in FIG. 1 (SEQ ID NO: 5) and the corresponding amino acid sequence in FIG. 2 (SEQ ID NO: 6).

Creating a genomic library

Genomic library for *S. suis* was created by digesting the isolated DNA from *S. suis* with restriction enzyme Sau 3A, and was then cloned to a suitable vector (Lambda GEM 11) and *E. coli* strain LE 392 was transformed. This library was screened with the PCR-product as a probe. The *S. suis* library can be screened also by one of the constructed oligonucleotides as a probe. The whole length adhesin gene was sequenced. Known nucleotide sequence can be selected for the construction of the two oligonucleotides, one of which is based to the N-terminal amino acid sequence.

Prepared oligonucleotides based on known nucleotide sequences of the protein (eg.) (II):

N-terminal oligonucleotide:
5' GCG TCT TTC AGC CCG 3' (SEQ ID NO: 7)
Corresponding amino acid sequence:

```
Ala Ser Phe Ser Pro
 7   8   9  10  11
```

The other oligonucleotide obtained:
5' CAG ATA GCG GAA CAC CTC 3' (SEQ ID NO: 8)

DNA amplification was carried out as described above, with the exception that step 3 was 56° C., 30 min, in the PCR program.

Specificity of the PCR procedure with oligonucleotides (II)

DNA amplification was carried out with DNA as a template from *S. suis* strain (628) and from *Streptococcus agalactiae* strains (strain B133 type III, strain 7217 type II, strain 4168 type I, obtained from Dr. Kyllikki Kunnas, National Public Health Laboratory, Kuopio) by using the PCR procedure and *S. suis* specific oligonucleotides (II). When *S. suis* strain was used as a template, a specific strong amplification product of about 370 bp was produced (which has been analysed to be part of the adhesin by sequencing as described above). When the DNA from *S. agalactiae* strains was used as a template, no clear amplification product was detected, and if detected they were of different size and very weak. Thus the PCR procedure can be considered specific for *S. suis* detection.

We claim:

1. A synthesized or isolated fragment of *Streptococcus suis* adhesin protein, which fragment comprises residues 1 to 11 from the amino acid sequence Ala-Ser-Pro-Ala-Glu-Ile-Ala-Ser-Phe-Ser-Pro-Xaa-Pro (SEQ ID NO: 2), wherein Xaa is alanine or arginine, and which fragment elicits antibodies that specifically bind to a *Streptococcus suis* adhesin protein having a molecular weight of about 18,000 and said protein binds to the Galα1-4Gal disaccharide structure.

2. The fragment according to claim 1, which is Ala-Ser-Pro-Ala-Glu-Ile-Ala-Ser-Phe-Ser-Pro-Xaa-Pro (SEQ ID NO: 2), wherein Xaa is alanine or arginine.

3. An immunoassay method of detecting antibodies to *Streptococcus suis* bacteria, comprising the steps of a) contacting a sample with the adhesin protein fragment according to claim 1, and b) analyzing the antigen-antibody complexes obtained, the formation of the antigen-antibody complexes indicating the presence or amount of antibodies to *Streptococcus suis* in the sample.

4. An immunogenic composition eliciting bactericidal antibodies comprising the adhesin protein fragment according to claim 1.

5. A synthesized or isolated fragment of *Streptococcus suis* adhesin protein which fragment elicits antibodies specifically binding to the *Streptococcus suis* adhesin protein encoded by SEQ ID NO: 5.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: protein (v) FRAGMENT TYPE: N-terminal (vi) ORIGINAL SOURCE:
        (A) ORGANISM: Streptococcus suis
        (B) STRAIN: 628, TEW/2, R75/L1, 825 and 752

(xi) SEQUENCE DESCRIPTION: SEQ ID NO: 1:

Ala Ser Pro Ala Glu Ile Ala Ser Phe Ser Pro Ala Pro Leu Ala
    1               5                   10                  15

(2) INFORMATION FOR SEQ ID NO: 2:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (v) FRAGMENT TYPE: N-terminal (vi) ORIGINAL SOURCE:
        (A) ORGANISM: Streptococcus suis (xi) SEQUENCE DESCRIPTION: SEQ ID NO: 2:

Ala Ser Pro Ala Glu Ile Ala Ser Phe Ser Pro Xaa Pro
    1               5                   10

(2) INFORMATION FOR SEQ ID NO: 3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: internal (vi) ORIGINAL SOURCE:
        (A) ORGANISM: Streptococcus suis (xi) SEQUENCE DESCRIPTION: SEQ ID NO: 3:

WSNCCNGCNG ARATNGC                                                    17

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (v) FRAGMENT TYPE: internal (vi) ORIGINAL SOURCE:
    (A) ORGANISM: Streptococcus suis (xi) SEQUENCE DESCRIPTION: SEQ ID NO: 4:

```
TCNGANACRT CRAANCC                                                  17
```

(2) INFORMATION FOR SEQ ID NO: 5:

(i) SEQUENCE CHARACTERISTICS:
        (A) LENGTH: 315 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus suis (xi) SEQUENCE DESCRIPTION: SEQ ID NO: 5:

```
GATTCTAAGG CTGTTTTGAA TCAAGCGGTG GCCGATTTAT CAGTAGCCCA TTCAATCCTC    60

CATCAAGTTC ACTGGTATAT GCGTGGTCGT GGCTTTATGA TTTGGCATCC AAAGATGGAT   120

GAATATATGG AAGAAATTGA TGGTTATTTG GATGAGATGA GTGAGCGTTT AATCACCTTA   180

GGTGGGGCAC CATTTTCTAC CCTTAAAGAG TTTAGTGAAA ATAGTCAGCT CAAGGAAGTT   240

CTTGGTGATT ACAATGTAAC GATTGAAGAG CAATTGGCGC GTGTGGTAGA GGTGTTCCGC   300

TATCTGGCTG CTCTT                                                   315
```

(2) INFORMATION FOR SEQ ID NO: 6:

(i) SEQUENCE CHARACTERISTICS:
        (A) LENGTH: 105 amino acids
        (B) TYPE: amino acid
        (C) STRANDEDNESS:
        (D) TOPOLOGY: unknown (ii) MOLECULE TYPE: protein (v) FRAGMENT TYPE: internal (vi) ORIGINAL SOURCE:
        (A) ORGANISM: Streptococcus suis (xi) SEQUENCE DESCRIPTION: SEQ ID NO: 6:

```
Asp Ser Lys Ala Val Leu Asn Gln Ala Val Ala Asp Leu Ser Val Ala
 1               5                  10                  15

His Ser Ile Leu His Gln Val His Trp Tyr Met Arg Gly Arg Gly Phe
                20                  25                  30

Met Ile Trp His Pro Lys Met Asp Glu Tyr Met Glu Glu Ile Asp Gly
            35                  40                  45

Tyr Leu Asp Glu Met Ser Glu Arg Leu Ile Thr Leu Gly Gly Ala Pro
        50                  55                  60

Phe Ser Thr Leu Lys Glu Phe Ser Glu Asn Ser Gln Leu Lys Glu Val
65                  70                  75                  80

Leu Gly Asp Tyr Asn Val Thr Ile Glu Glu Gln Leu Ala Arg Val Val
                85                  90                  95

Glu Val Phe Arg Tyr Leu Ala Ala Leu
                100                 105
```

(2) INFORMATION FOR SEQ ID NO: 7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: internal (vi) ORIGINAL SOURCE:
        (A) ORGANISM: Streptococcus suis (xi) SEQUENCE DESCRIPTION: SEQ ID NO: 7:

GCGTCTTTCA GCCCG                                                15

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(v) FRAGMENT TYPE: internal (vi) ORIGINAL SOURCE:
        (A) ORGANISM: Streptococcus suis (xi) SEQUENCE DESCRIPTION: SEQ ID NO: 8:

CAGATAGCGG AACACCTC                                             18